United States Patent
Stewart et al.

(10) Patent No.: US 8,448,949 B2
(45) Date of Patent: May 28, 2013

(54) SEALING ASSEMBLY WITH INTEGRAL SENSOR

(75) Inventors: Shelby F. Stewart, Parksville, KY (US); Shonda Peters, Georgetown, KY (US); Eric J. Banks, Richmond, KY (US); Kevin M. Pascal, Lexington, KY (US)

(73) Assignee: Parker-Hannifin Corporation, Cleveland, OH (US)

( * ) Notice: Subject to any disclaimer, the term of this patent is extended or adjusted under 35 U.S.C. 154(b) by 0 days.

(21) Appl. No.: 13/384,612

(22) PCT Filed: Aug. 12, 2010

(86) PCT No.: PCT/US2010/045286
§ 371 (c)(1),
(2), (4) Date: Jan. 18, 2012

(87) PCT Pub. No.: WO2011/019888
PCT Pub. Date: Feb. 17, 2011

(65) Prior Publication Data
US 2012/0119448 A1    May 17, 2012

Related U.S. Application Data

(60) Provisional application No. 61/233,530, filed on Aug. 13, 2009, provisional application No. 61/329,640, filed on Apr. 30, 2010.

(51) Int. Cl.
*F16J 3/00*     (2006.01)
*F16J 15/02*    (2006.01)
*F16J 15/08*    (2006.01)
*F16L 17/06*    (2006.01)

(52) U.S. Cl.
USPC ............ 277/317; 277/609; 277/630; 277/654

(58) Field of Classification Search
CPC ........ F16J 15/064; F16J 15/061; F16J 15/0887
USPC .................. 277/317, 609, 630, 654
See application file for complete search history.

(56) References Cited

U.S. PATENT DOCUMENTS

| 2,407,076 A | 9/1944 | Harkness |
| 2,783,295 A | 2/1957 | Ewing |

(Continued)

FOREIGN PATENT DOCUMENTS

| DE | 30 06 656 | * | 9/1981 |
| DE | 30 06 656 A1 | | 9/1981 |

(Continued)

OTHER PUBLICATIONS

International Search Report and the Written Opinion for corresponding International Application No. PCT/US2010/045286 mailed Nov. 15, 2010.

(Continued)

*Primary Examiner* — Vishal Patel
*Assistant Examiner* — Nathan Cumar
(74) *Attorney, Agent, or Firm* — Renner, Otto, Boisselle & Sklar, LLP

(57) ABSTRACT

A sealing assembly is equipped with life-sensing means in terms of wear (12*a*, 12*b*), thermal degradation, physical damage, chemical incompatibility and structural breakdowns within the sealing assembly, and means (22*a, b*) for transmitting an output of the sensing means to detect a change in the sealing environment or an impending seal failure.

11 Claims, 8 Drawing Sheets

U.S. PATENT DOCUMENTS

| | | | |
|---|---|---|---|
| 2,796,457 A | 6/1957 | Stinger | |
| 3,019,281 A | 1/1962 | Hartwell | |
| 3,247,312 A | 4/1966 | Alessi | |
| 3,372,226 A | 3/1968 | Sewell | |
| 3,783,173 A * | 1/1974 | Twomey | 174/356 |
| 3,873,102 A | 3/1975 | Lotze et al. | |
| 4,677,373 A * | 6/1987 | Kobayashi et al. | 324/700 |
| 4,825,015 A | 4/1989 | Prott et al. | |
| 5,107,071 A | 4/1992 | Nakagawa | |
| 5,246,235 A | 9/1993 | Heinzen | |
| 5,540,448 A | 7/1996 | Heinzen | |
| 5,702,111 A | 12/1997 | Smith | |
| 5,865,971 A | 2/1999 | Sunkara | |
| 6,708,984 B1 | 3/2004 | North et al. | |
| 7,316,154 B1 | 1/2008 | Bennett | |
| 7,488,010 B2 | 2/2009 | Wellman et al. | |
| 7,498,703 B2 | 3/2009 | Rea, Sr. et al. | |
| 7,555,936 B2 | 7/2009 | Deckard | |
| 7,752,904 B2 | 7/2010 | Krutz et al. | |
| 2003/0042688 A1 * | 3/2003 | Davie et al. | 277/590 |
| 2006/0145429 A1 * | 7/2006 | Casler et al. | 277/627 |
| 2006/0220498 A1 * | 10/2006 | Kremer | 310/338 |
| 2007/0131035 A1 | 6/2007 | Krutz et al. | |

FOREIGN PATENT DOCUMENTS

| | | |
|---|---|---|
| WO | 2005/031195 A1 | 4/2005 |
| WO | 2009/088505 | 7/2009 |

OTHER PUBLICATIONS

International Preliminary Report on Patentability for corresponding International Application No. PCT/US2010/045286 mailed Nov. 9, 2011.

* cited by examiner

SEALING ASSEMBLY WITH INTEGRAL SENSOR

RELATED APPLICATIONS

This application is a national phase of International Application No. PCT/US2010/045286 filed Aug. 12, 2010 and published in the English language, which claims priority to U.S. 61/233,530 filed Aug. 13, 2009 and U.S. 61/329,640 filed Apr. 30, 2010.

FIELD

The invention relates generally to a sealing assembly, and more particularly to a sealing assembly that is equipped with life-sensing means in terms of wear, thermal degradation, physical damage, chemical incompatibility and structural breakdowns within the sealing assembly, and means for transmitting an output of the sensing means to detect a change in the sealing environment or an impending seal failure.

BACKGROUND

Providing a seal between adjacent surfaces of an assembly is necessary to prevent a leak when the hardware and its mating part are conducting or containing media. Such seals are typically made of, but not limited to, thermosetting or thermoplastic polymer materials, which are relatively resilient and deformable. The seal is generally annular and has a circular cross-section, but could also include any other engineered shape configured for sealing. The hardware may have a groove in its front face for receiving the seal, or the seal may be overmolded directly onto the hardware. When the hardware is properly connected to its mating part, the seal is compressed by the adjacent face surface of the mating part. A seal may be housed in the hardware for extended periods of time.

The seal assembly may be used in a hostile environment where the seal is subjected to aggressive chemicals, extreme temperatures, and/or high pressure. Such conditions may cause the seal to deteriorate. In addition, the seal may be improperly installed or may be physically damaged which may cause the seal to malfunction.

Seal malfunction can cause both minor and catastrophic equipment failures. Down time, maintenance and repair costs could be minimized by the ability to sense impaired operational performance or impending failure in an elastomeric seal.

SUMMARY

The present invention is directed to sealing assemblies, and particularly to a sealing assembly with integrated life-sensing capability for detecting structural breakdowns and environmental changes within the sealing assembly. Such sealing assembly may find particular use in applications from the automotive, heavy duty, general industrial, consumer products, fluid power, aerospace, microelectronics, energy systems, oil and gas, life sciences and chemical processing markets.

In an illustrative embodiment of the invention, a sealing assembly with integrated sensing capability includes a seal member that includes first and second conductive layers and an intermediate layer therebetween, the intermediate layer being formed of a dielectric material such that the first, second and intermediate layers form in combination a capacitive element having a capacitance associated therewith. The sealing assembly also includes a first electrical contact to the first conductive member, a second electrical contact to the second conductive member, and an insulator between the first and second electrical contacts. The sealing assembly of this embodiment further includes a first plate having first central passage therethrough and a first inner sealing contact surface; and a second plate having a second central passage therethrough and a second inner sealing contact surface; the seal member located between the first plate and the second plate to form a seal therebetween.

In one embodiment, the seal member may further include a second dielectric layer and a third conductive layer between the first and second conductive layers to form a capacitive element having alternating conductive and dielectric layers.

The conductive layers of the seal member may be constructed of a thermosetting or thermoplastic polymer material and electrically conductive filler. The dielectric layer of the seal member may be constructed of a thermosetting or thermoplastic polymer. The polymer of the dielectric layer may also include electrically insulating filler. The first and second plates may be constructed of an electrically insulating polymeric material.

In one aspect of the invention, the first plate of the sealing assembly has a first conductive element on the first inner sealing contact surface and the second plate has a second conductive element on the second inner sealing contact surface, the first conductive layer of the seal member electrically contacting the first conductive element of the first plate and the second conductive layer of the seal member electrically contacting the second conductive element of the second plate.

The conductive elements of the first and second plates may be inlaid into the inner sealing surface of the first and second plates, respectively. In another embodiment, the conductive element of the first and second plates is a conductive film deposited on the inner sealing surface of the first and second plates, respectively.

In one embodiment, the insulator between the first and second electrical contacts is a spacer having a central bore into which the seal member is seated, the spacer positioned between the first and second plates.

In another aspect of the invention, the first conductive layer of the seal member includes an outwardly extending first tab for making electrical contact with the first conductive layer, and the second conductive layer of the seal member includes an outwardly extending second tab for making electrical contact with the second conductive layer. The sealing assembly may further include an insulating spacer into which the seal member is seated, the spacer having a channel therein, the channel having a first side and a second side and a girder between the first and second sides, the girder positioned between the first tab and the second tab of the seal member.

In another illustrative embodiment of the invention, a sealing assembly with integrated sensing capability includes a seal member including first and second conductive layers and an intermediate layer therebetween, the intermediate layer being formed of a dielectric material such that the first, second and intermediate layers form in combination a capacitive element having a capacitance associated therewith. The first conductive layer of the seal member may include an outwardly extending first tab for making electrical contact with the first conductive layer, and the second conductive layer of the seal member may include an outwardly extending second tab for making electrical contact with the second conductive layer. The sealing assembly may further include an electrically insulating frame into which the seal member is seated, the frame having a channel therein, the channel having a first side and a second side and a girder between the first and second sides, the girder positioned between the first tab and the second tab of the seal member. The sealing assembly of this embodiment is configured to provide a seal between a non-conductive hardware component and a second non-conductive mating component.

The capacitive element of the sealing assembly may be electrically connected to means for sensing changes in the capacitance presented by the seal member between the first conductive element and the second conductive element.

In one embodiment, the capacitive element is configured to sense at least one of load conditions, wear, thermal degradation, physical damage and chemical incompatibility, and is coupled to data processing circuitry adapted to signal that a structural failure of the seal is impending.

The foregoing and other features of the invention are hereinafter described in greater detail in accordance with reference to the accompanying drawings.

DETAILED DESCRIPTION

The present invention is directed to a sealing assembly having an integral sensor that is capable of capturing and responding to physical and chemical changes within the seal assembly. The seal within the sealing assembly functions as its own heath and life sensor. The seal includes conductive layers separated by dielectric layers to form one or more capacitive elements by which changes in capacitance can be sensed. As the seal wears, changes in the dielectric constant can occur, as do the physical properties of the conductive and dielectric layers that can also affect the capacitance of the seal. The layers of the seal are configured to enable sensing of load conditions, damage to the seal, chemical incompatibility within the seal environment and improper mounting conditions. The layers of seal can be coupled to data processing circuitry capable of predicting when a structural failure of the seal will occur, so that the seal can be safely used for its full life and then replaced before any damage occurs to any system containing the seal or to any objects surrounding the sealing assembly.

Figure 1:
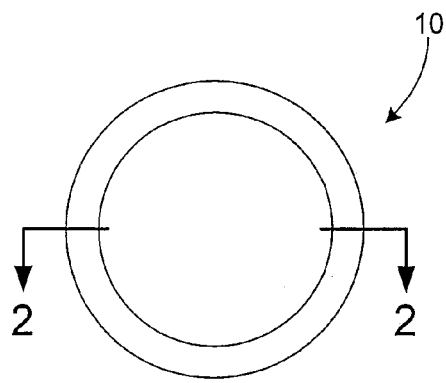
FIG. 1 is a top view of a capacitor seal ring in accordance with the present invention.
Figure 2:
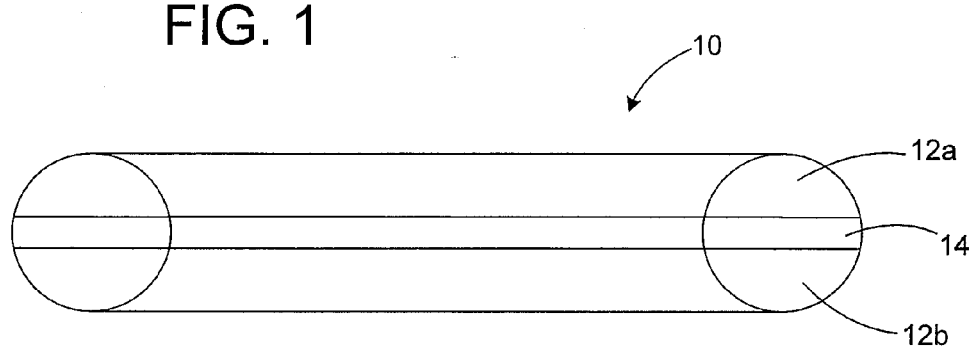
FIG. 2 is a cross-sectional view of an exemplary embodiment of the capacitor seal ring of FIG. 1, wherein the seal ring has a three-layer structure.
Figure 2A:
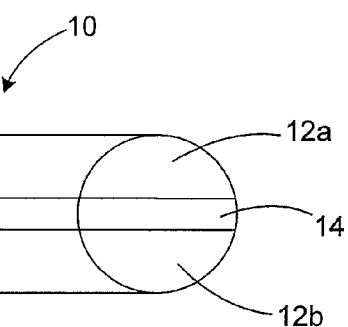
FIG. 2A is an end view of the seal ring of FIG. 2.

Referring to the drawings, and initially to FIGS. 1 to 2A, a capacitor seal ring 10 has a three layer laminate structure that includes a pair of conductive layers 12a and 12b separated by an intermediate dielectric layer 14. The three layers in combination form an electrical element, namely, a capacitive element.

The dielectric layer 14 may be constructed of a thermosetting elastomer, such as, for example, acrylonitrile butadiene (NBR); fluoroelastomers (FKM) including hexafluoropropylene, vinylidenefluoride, tetrafluoroethylene and perfluoromethylvinylether copolymers; hydrogenated copolymers of acrylonitrile and butadiene monomers (HNBR); silicone rubber (VMQ), including dimethylpolysiloxane; or fluorinated silicone rubber (FVMQ), including analogs of dimethylpolysiloxane. The dielectric layer 14 may also be constructed of a thermoplastic elastomer, such as, for example, styrenic block copolymers, polyolefinic blends, elastomeric alloys, polyurethanes, copolyesters and polyamides.

The dielectric layer 14 may be compounded with any one of the thermosetting or thermoplastic elastomers into a suitable formulation by the addition of process aids, curatives and fillers to reinforce or otherwise modify the properties of the compound. Illustrative examples of suitable fillers for obtaining the desired dielectric properties include barium sulfate, clays, fume process silicas, and combinations of one or more thereof. Preferably, the compound used to form the dielectric layer 14 has a dielectric constant of at least 5.0 at 1 kHz. More preferably, the compound of the dielectric layer 14 has a dielectric constant of at least 10.0 at 1 kHz.

The conductive layers 12a and 12b may be constructed of a thermosetting elastomer, such as, for example, acrylonitrile butadiene (NBR); fluoroelastomers (FKM) including hexafluoropropylene, vinylidenefluoride, tetrafluoroethylene and perfluoromethylvinylether copolymers; hydrogenated copolymers of acrylonitrile and butadiene monomers (HNBR); silicone rubber (VMQ), including dimethylpolysiloxane; fluorinated silicone rubber (FVMQ), including analogs of dimethylpolysiloxane; or terpolymers of ethylene propylene diene monomers (EPDM). The conductive layers may also be constructed of a thermoplastic elastomer, such as those listed above. The conductive layers 12a and 12b are compounded with one or more of the foregoing elastomers into a usable formulation by the addition of process aids, curatives and fillers to reinforce or otherwise modify the properties of the compound. Examples of suitable fillers for obtaining the desired conductive properties include carbon black, indium tin oxide, carbon nano-tubes, and graphite. In one embodiment, the volume resistivity of the compound is in the range of about $10^5$ ohm-cm to about $10^8$ ohm-cm.

Figure 3:
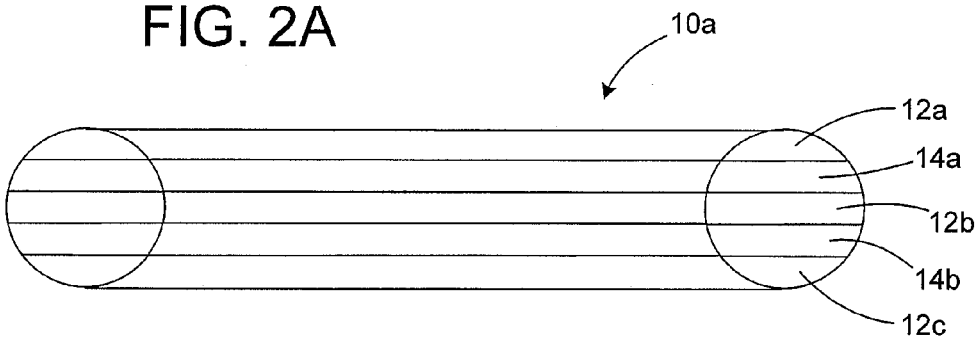
FIG. 3 is a cross-sectional view of an exemplary embodiment of the capacitor seal ring of the present invention wherein the seal ring has a five-layer structure.
Figure 3A:
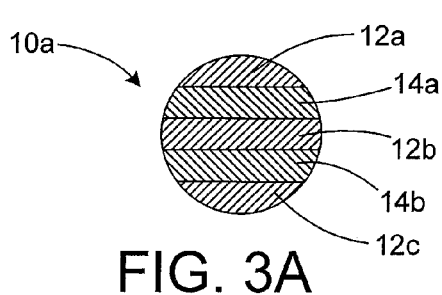
FIG. 3A is an end view of the seal ring of FIG. 3.

Referring to FIGS. 3 and 3A, the capacitor seal ring 10a has a five-layer laminate structure that includes conductive layers 12a, 12b and 12c, separated by dielectric layers 14a and 14b. The materials used to construct the three conductive layers and two dielectric layers may include those materials listed above with regard to the three-layer assembly.

The capacitor seal ring may be constructed by cold molding the dielectric and conductive layers independently of one another. The cold molding process involves heating the respective material to a temperature that is high enough to enable the material to flow, yet not high enough to initiate the curing process. The cold molded dielectric and conductive layers are assembled in an alternating arrangement and then subjected to a curing process to form the laminate elastomeric seal.

The performance and condition of the seal ring 10 can be monitored by positioning the seal ring 10 within a seal assembly and applying an electric current to one of the conductive layers to measure changes in capacitance. Electrical connection to the conductive layers 12a and 12b of the seal may be made through flanges configured specifically for this purpose.

Figure 4:
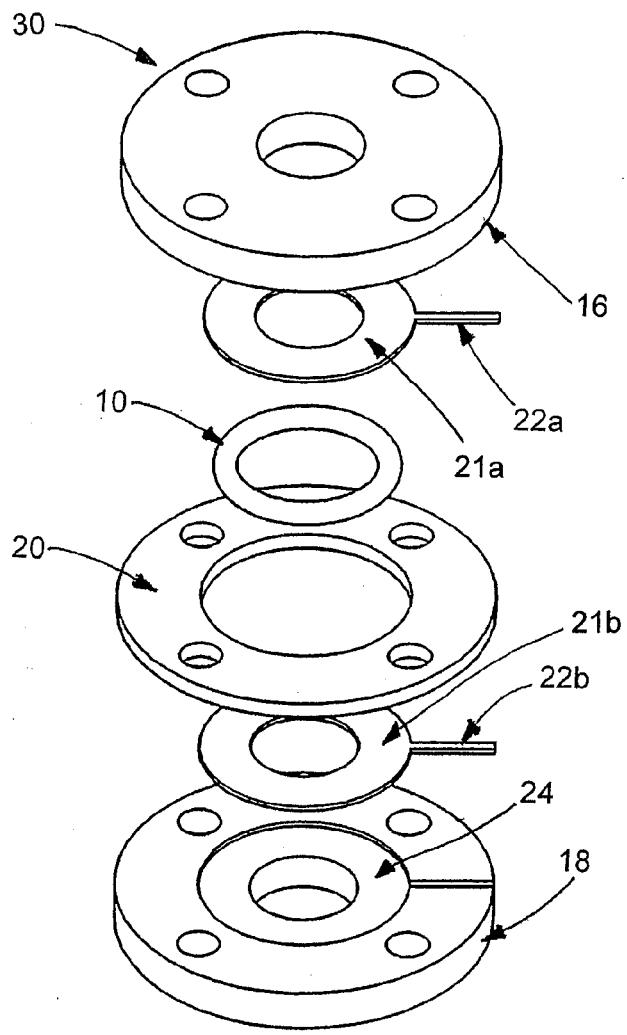
FIG. 4 is a perspective exploded view of an exemplary embodiment of a sealing assembly incorporating a conductive inlay and the capacitor seal ring in accordance with the present invention.
Figure 5:
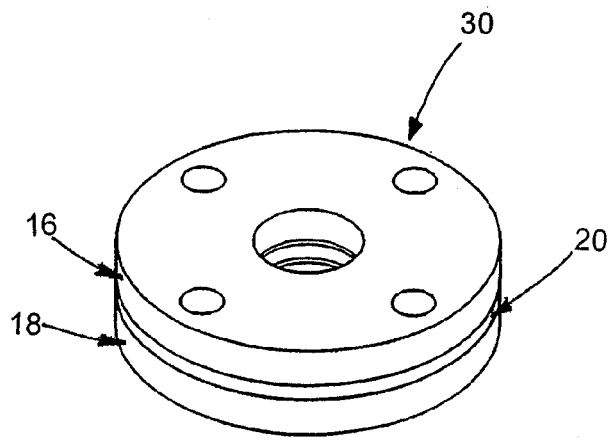
FIG. 5 is an assembled view of the sealing assembly of FIG. 4.

Referring to FIGS. 4 and 5, a seal assembly 30 includes an electrically insulating upper plate 16, an electrically insulating lower plate 18 and a spacer 20 positioned between the upper plate 16 and the lower plate 18. Each of the upper plate 16, lower plate 18 and spacer 20 has a central passage therethrough. The capacitor seal ring 10 is seated within the central opening of the spacer 20. Conductive inlay 21b fits within a complementary recess 24 in lower plate 18 that surrounds the central passage, and makes direct electrical contact with the second conductive layer 12b of seal ring 10. Conductive inlay 21b includes a lead 22b for making electrical contact with a sensor circuit (not shown). Upper plate 16 also includes a complementary recess (not visible in figure view) that surrounds the central passage of upper plate 16 into which conductive inlay 21a fits to make direct electrical contact with the first conductive layer 12a of seal ring 10. Conductive inlay 21a includes a lead 22a for making electrical contact with the sensor circuit.

The upper plate 16, lower plate 18, and spacer 20 may be independently constructed from an insulating material such as plastic. Non-limiting examples of such insulating plastics include polyoxymethylene (Delrin® available from DuPont); polyether ether ketone (PEEK); polytetrafluoroethylene (PTFE); VESPEL® polyimide available from DuPont; RULON® polytetrafluoroethylene-based resins available from Saint-Gobain; and KAPTON® polyimide available from DuPont.

Conductive inlays 21a and 21b may be constructive from a conductive metal or metal alloy, such as, for example, copper, brass, bronze, or stainless steel. Conductive inlays 21a and 21b are appropriately shaped based on the geometry of the seal, each with a stem-like extension 22a, 22b that serves as the connection point to a circuit for measuring the capacitance and capacitance changes of the seal ring 10. Electrical connection to the conductive inlays may be permanent, such as by soldering, or may be achieved by temporary or removable means, such as by a clip or fastener type connection.

Figure 6:
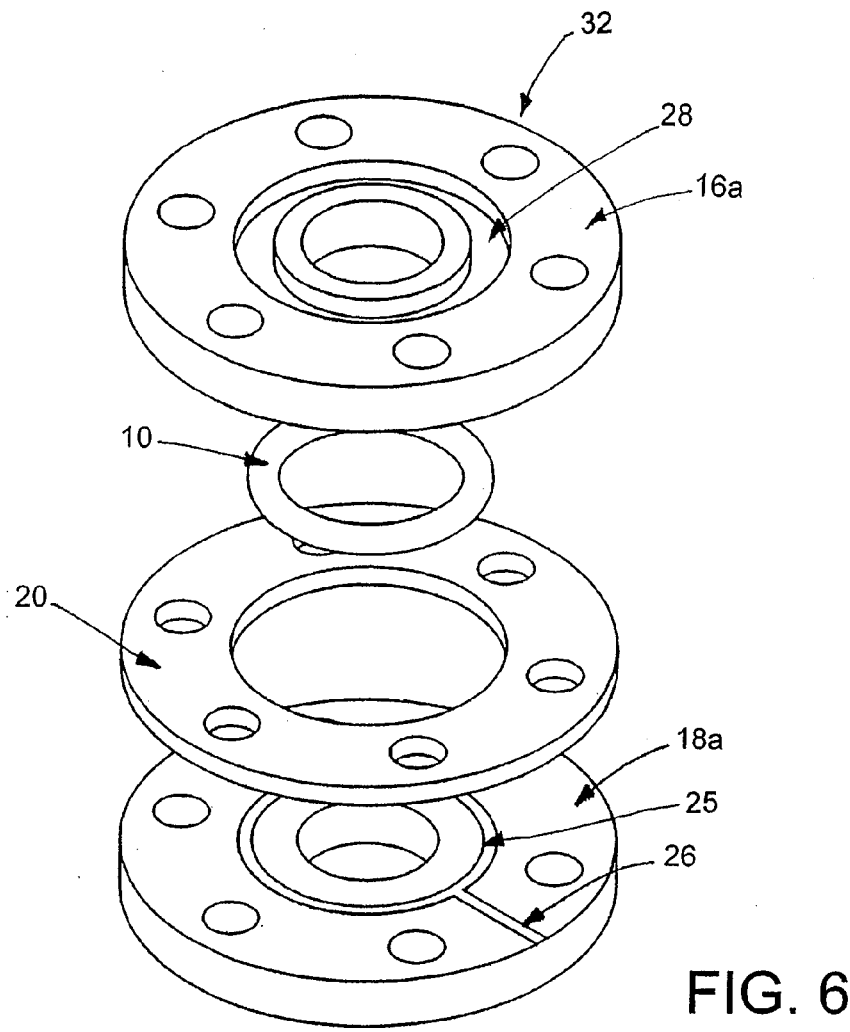
FIG. 6 is a perspective exploded view of another exemplary embodiment of a sealing assembly incorporating a plated conductive layer and the capacitor seal ring in accordance with the present invention.
Figure 7:
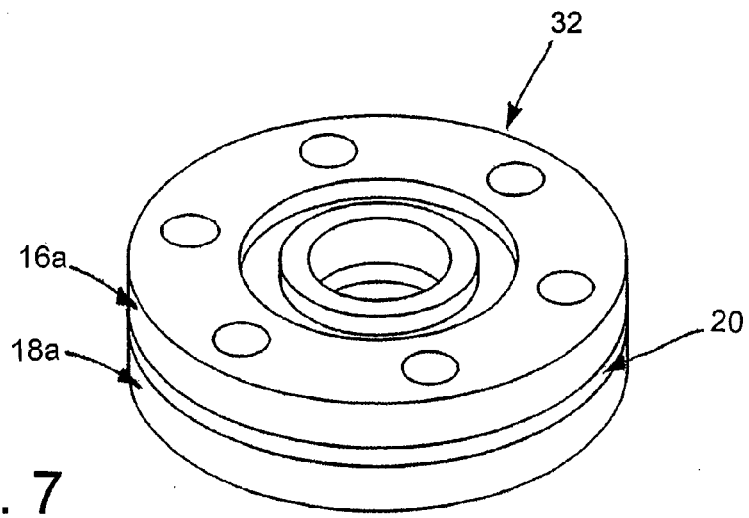
FIG. 7 is an assembled view of the sealing assembly of FIG. 6.

In FIGS. 6 and 7, another embodiment of a seal assembly is shown as 32, which is similar to seal assembly 30, with the exception that a conductive film 25 is deposited onto the inner surface of lower plate 18a to make electrical contact with seal ring 10, rather than a conductive inlay. The conductive film 25 is generally ring shaped with a stem-like extension 26 that serves as the connection point to a circuit for measuring the capacitance and capacitance changes of the seal ring 10. Upper plate 16a also includes a conductive film deposited onto the inner surface of upper plate 16a (not visible in figure view) for making electrical contact with seal ring 10. Upper plate 16a may include a groove 28 on its outer surface, into which a seal may be seated. This additional groove may be incorporated into any of the embodiments described herein as necessary to the requirements of the application in which the sealing assembly is to be used.

Figure 9:
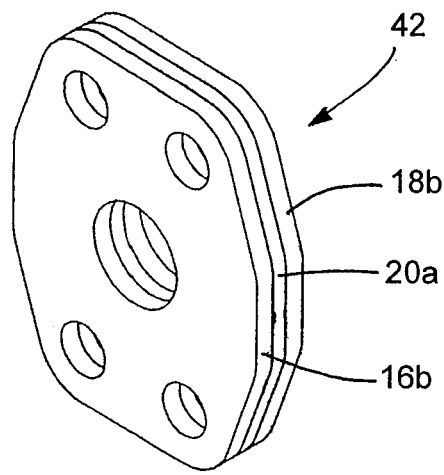
FIG. 9 is an assembled view of the sealing assembly of FIG. 8.
Figure 8:
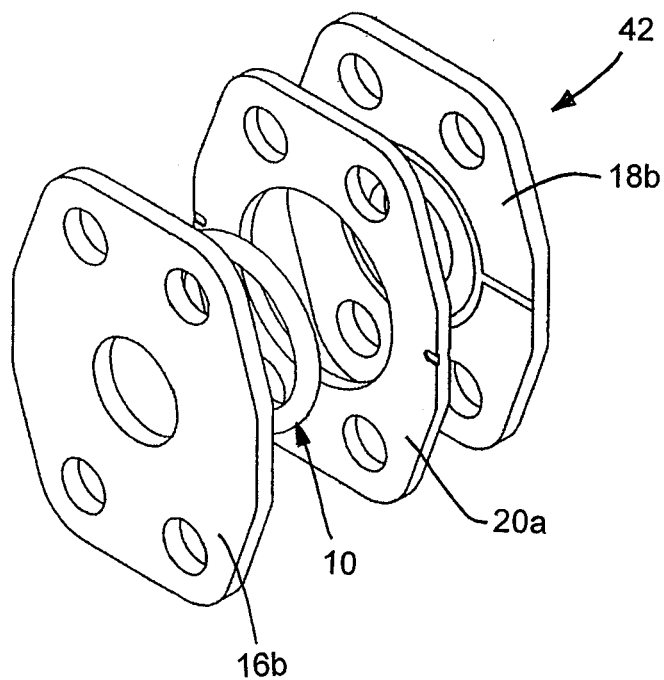
FIG. 8 is a perspective exploded view of another exemplary embodiment of a sealing assembly of the present invention that conforms with a standard code 61/62 style flange assembly.

In FIGS. 8 and 9, another embodiment of a seal assembly is shown as 42, which is similar to seal assembly 32, with the exception that the overall shape of the assembly is not annular. Instead, the seal assembly 42 has a shape that conforms with a standard code 61/62 style flange assembly. Seal assembly 42 includes an electrically insulating upper plate 16b, an electrically insulating lower plate 18b and a spacer 20a positioned between the upper plate 16b and the lower plate 18b. The capacitor seal ring 10 is seated within the central opening of the spacer 20a.

Figure 10A:
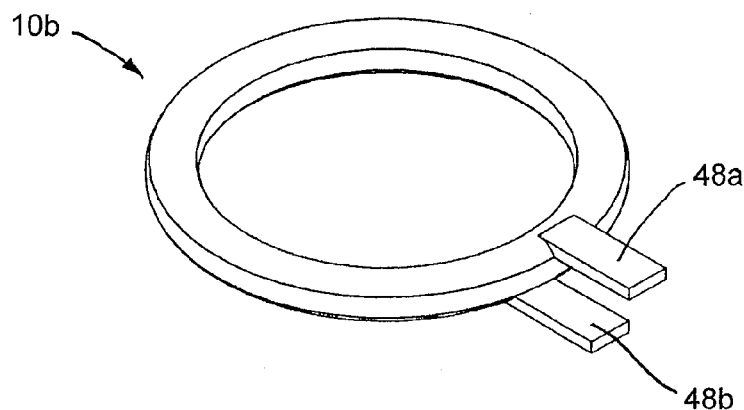
FIGS. 10A-10C are perspective, top and cross-sectional views, respectively, of another exemplary embodiment of a capacitor seal ring having integral connection points.
Figure 10B:
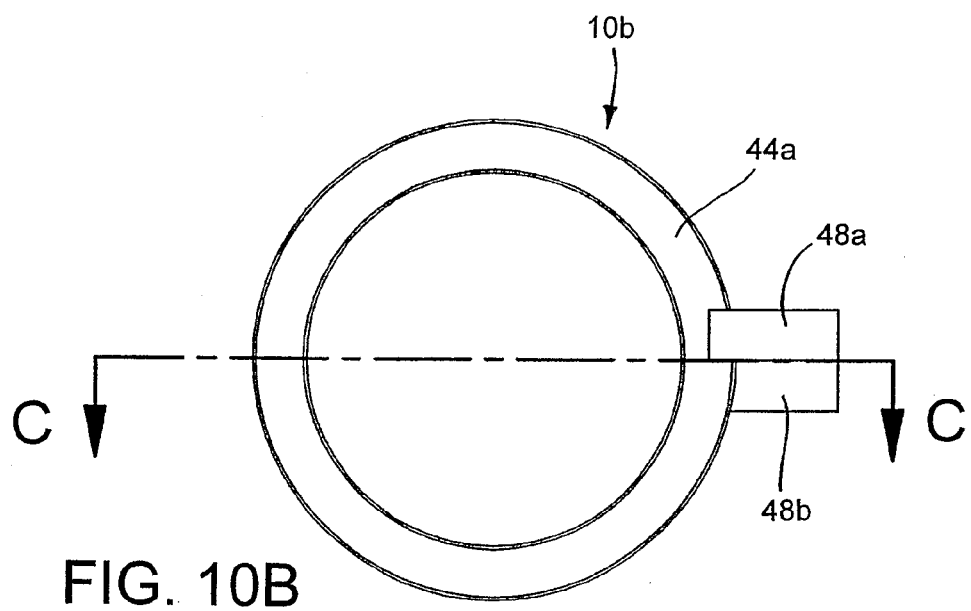
Figure 10C:
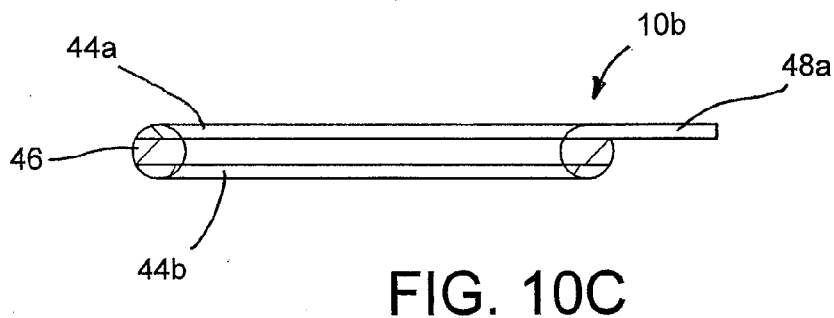

Referring to FIGS. 10A-10C, another embodiment of the capacitor seal is illustrated. Capacitor seal 10b has a three layer laminate structure that includes a pair of conductive layers 44a and 44b separated by an intermediate dielectric layer 46. Each of the conductive layers 44a and 44b is molded with a tab 48a, 48b, respectively, extending outwardly from the main body of the ring that serves as the connection point to a circuit for measuring the capacitance and capacitance changes of the seal ring 10b. By forming the electrical connection from the material of the conductive layers, separate conductive pathway(s) in the seal assembly (as embodied by inlays 21a and 21b in FIG. 4, and conductive film 25 in FIG. 6) may not be required. While the tabs 48a and 48b are shown as having a rectangular shape, the tabs are not limited in shape and may be any shape suitable for making electrical connection to the ring 10b.

Figure 11:
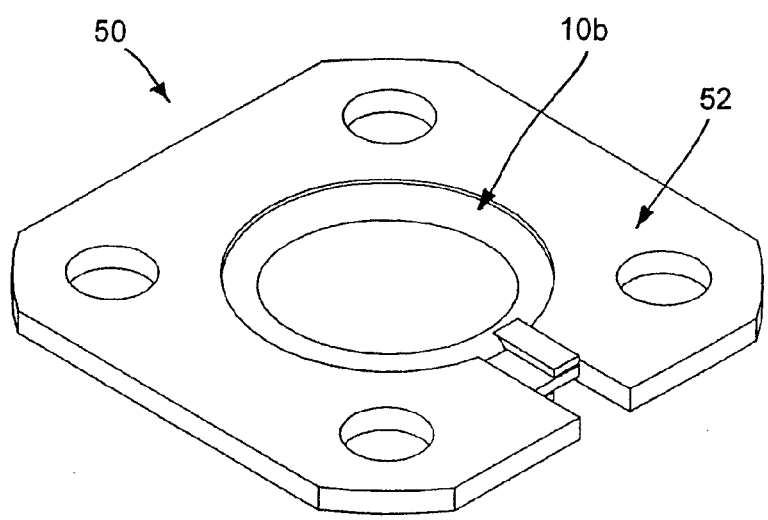
FIG. 11 is a perspective view of an exemplary seal assembly incorporating the capacitor seal ring of FIGS. 10A-10C.
Figure 12:
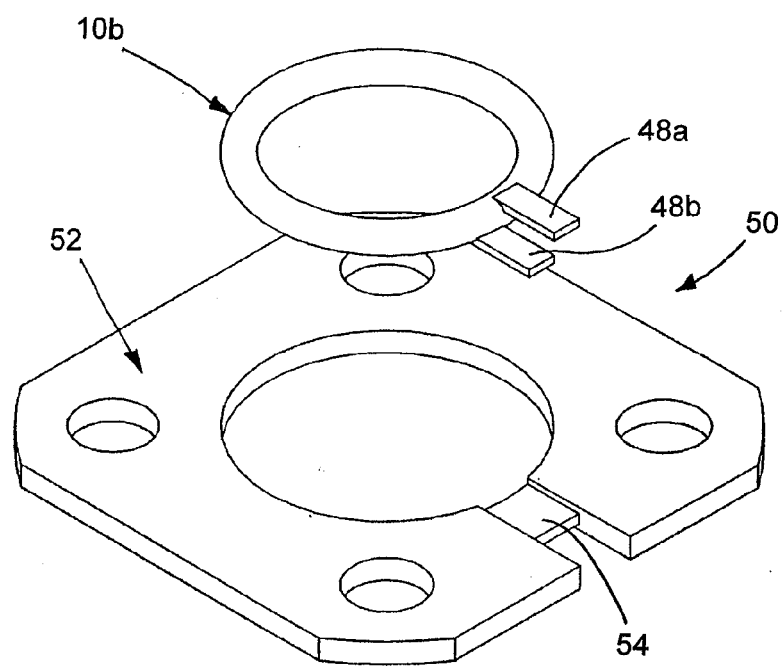
FIG. 12 is an exploded view of the seal assembly of FIG. 11.

In FIGS. 11 and 12, seal assembly 50, incorporating seal 10b, illustrates a simplified assembly for use with mating hardware that is non-conductive. Seal assembly 50 includes insulating spacer 52 having a central opening into which seal 10b is seated, such that spacer 52 frames seal 10b. Spacer 52 includes a bridged channel that forms an H-shaped girder 54. Non-conductive girder 54 is positioned between tab 48a and 48b when the seal 10b is seated in the spacer 52 to provide access to the tabs and enable electrical connections to be made to the tabs.

Figure 13:
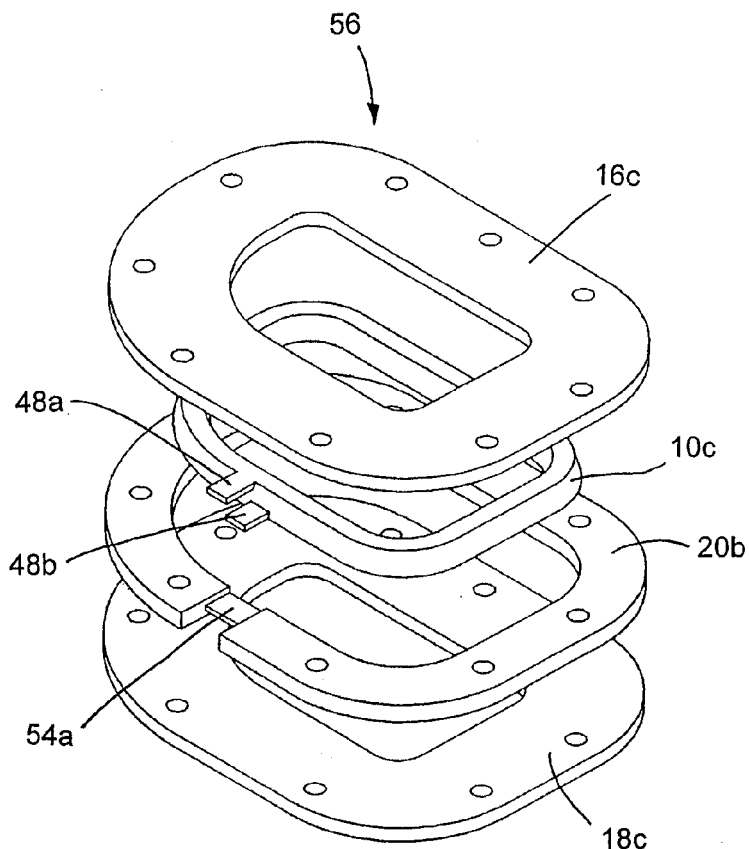
FIG. 13 is an exploded view of an exemplary seal assembly for use with conductive mating hardware, and which incorporates the capacitor seal ring of FIGS. 10A-10C.
Figure 14:
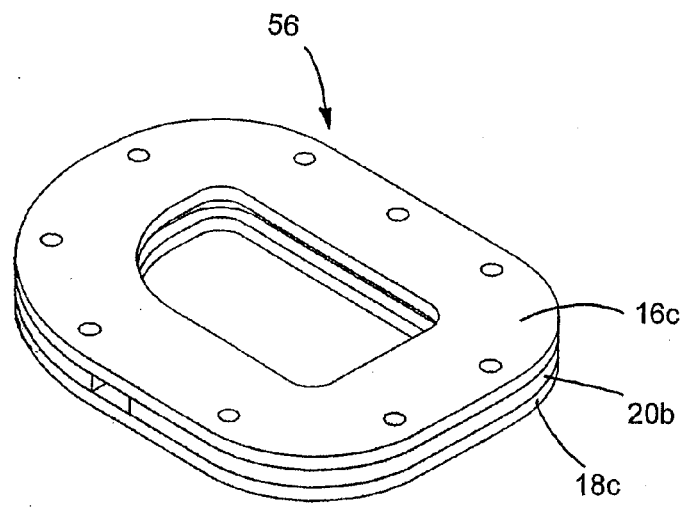
FIG. 14 is an assembled view of the sealing assembly of FIG. 13.

Referring to FIGS. 13 and 14, another embodiment of a seal assembly is shown as 56. The overall shape of seal assembly 56 is not annular and the shape of the capacitor seal 10c is not annular. Although illustrated here as having a trapezoidal shaped cross-section, seal 10c may have any shape suitable for providing sealing in the particular application in which it is used. Seal assembly 56 includes an electrically insulating upper plate 16c, an electrically insulating lower plate 18c and a spacer 20b positioned between the upper plate 16c and the lower plate 18c. The capacitor seal 10c is similar to capacitor seal 10b in that it includes integrated tabs 48a and 48b extending from the main body of the seal. Seal 10c is seated within the inner bore of the spacer 20b. Spacer 20b includes a bridged channel that forms an H-shaped girder 54a. Non-conductive girder 54a is positioned between tabs 48a and 48b when the seal 10c is seated in the spacer 20b to provide access to the tabs and enable electrical connections to be made to the tabs.

The sealing assembly is electrically connected to a circuit for sensing changes in the capacitance associated with the seal 10 resulting from distortion or damage to the seal. According to one aspect of the invention, an acceptable range is established for the capacitance and a signal is generated that a structural failure of the seal is impending in response to the capacitance deviating outside the acceptable range. The electrical monitoring of the condition of the seal, and in particular, monitoring the electrical capacitance with respect to a pre-established acceptable range enables accurate predictions of seal failure or environmental changes.

Figure 15:
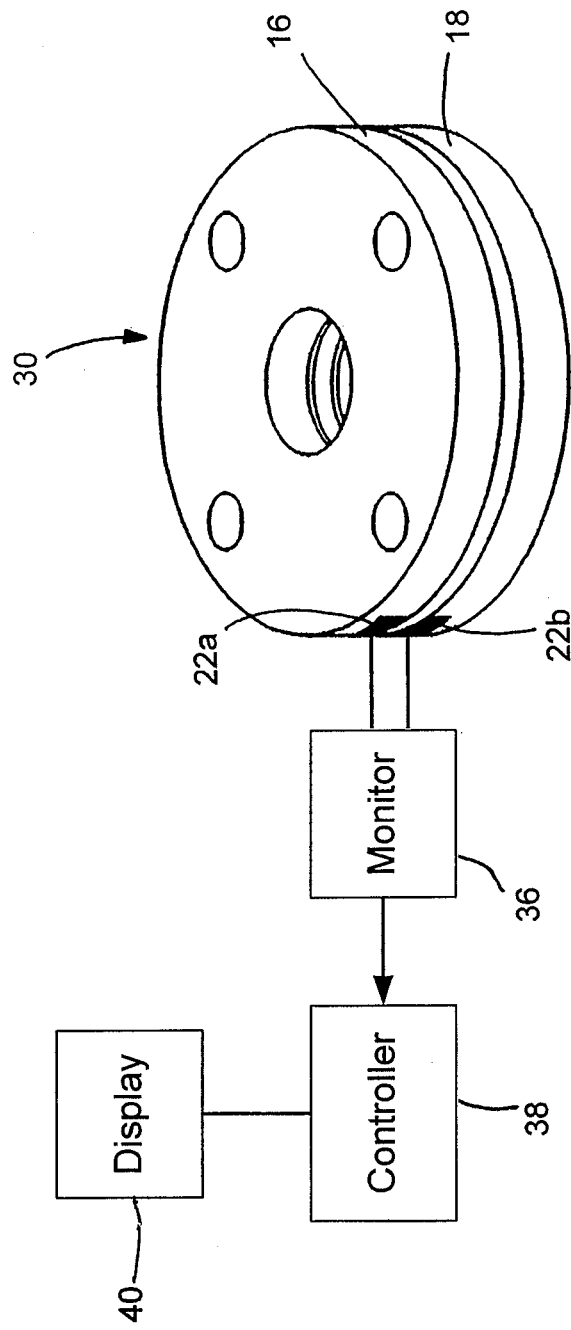
FIG. 15 shows an embodiment of the sealing assembly as connected to a monitoring system.

Referring to FIG. 15, a sealing assembly 30 includes electrical leads 22a and 22b, which are electrically connected to the outer conductive layers of seal 10 (not visible in figure view). An acceptable range for the electrical capacitance of the capacitive coupling (e.g., based on an initial capacitance reading obtained from the seal) is first determined. By providing a suitably configured monitor 36, changes in the electrical capacitance of the capacitive seal 10 (formed by the conductive layer 12a, the dielectric layer 14 and the conductive layer 12b) can therefore be sensed. Monitor 36 may sense changes in capacitance by including the capacitance presented by the seal as part of a resonant circuit and detecting variations in the frequency to determine changes in capacitance. A system for predicting the malfunction or deterioration of the seal includes controller 38 programmed to carry out the operations described herein. Display 40 can display a signal that structural failure of the seal 10 is impending in view of the capacitive value deviating outside the acceptable range.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sealing assembly with integrated sensing capability comprising:
    a seal member including first and second conductive layers and an intermediate layer there between, the intermediate layer being formed of a dielectric material such that the first, second and intermediate layers form in combination a capacitive element having a capacitance associated therewith;
    a first plate having a first central passage there through, a first inner sealing contact surface, and a first conductive element inlaid into the first inner sealing contact surface and surrounding the first central passage, wherein the first conductive element is in contact with the first conductive layer of the seal member;
    a second plate having a second central passage there through, a second inner sealing contact surface, and a second conductive element inlaid into the second inner sealing contact surface and surrounding the second central passage, wherein the second conductive element is in contact with the second conductive layer of the seal member;
    the seal member located between the first plate and the second plate and surrounding the first and second central passages to form a seal between the first and second plates;
    an insulator between the first and second conductive elements comprising a spacer having a central bore into which the seal member is seated, the spacer positioned between the first and second plates.

2. The sealing assembly of claim 1 wherein the seal member further includes a second dielectric layer and a third conductive layer between the first and second conductive layers to form a capacitive element having alternating conductive and dielectric layers.

3. The sealing assembly of claim 1 wherein the conductive layers of the seal member independently comprise a thermosetting or thermoplastic polymer material and electrically conductive filler.

4. The sealing assembly of claim 1 wherein the dielectric layer of the seal member comprises a thermosetting or thermoplastic polymer.

5. The sealing assembly of claim 4 wherein the dielectric layer further comprises electrically insulating filler.

6. The sealing assembly of claim 1 wherein the first and second plates are constructed of an electrically insulating material.

7. The sealing assembly of claim 1 wherein the first conductive layer of the seal member includes an outwardly extending first tab for making electrical contact with the first conductive layer, and the second conductive layer of the seal member includes an outwardly extending second tab for making electrical contact with the second conductive layer.

8. The sealing assembly of claim 7 wherein the spacer has a channel therein, the channel having a first side and a second side and a girder between the first and second sides, the girder positioned between the first tab and the second tab of the seal member.

9. A sealing assembly with integrated sensing capability comprising:
    a seal member including first and second conductive layers and an intermediate layer therebetween, the intermediate layer being formed of a dielectric material such that the first, second and intermediate layers form in combination a capacitive element having a capacitance associated therewith, wherein the first conductive layer of the seal member includes an outwardly extending first tab for making electrical contact with the first conductive layer, and the second conductive layer of the seal member includes an outwardly extending second tab for making electrical contact with the second conductive layer; and
    an electrically insulating frame into which the seal member is seated, the frame having a channel therein, the channel having a first side and a second side and a girder between the first and second sides, the girder positioned between the first tab and the second tab of the seal member;
    wherein the sealing assembly is configured to provide a seal between a non-conductive hardware component and a second non-conductive mating component.

10. The sealing assembly of claim 1 wherein the capacitive element is electrically connected to means for sensing changes in the capacitance presented by the seal member between the first conductive element and the second conductive element.

11. The sealing assembly of claim 1 wherein the capacitive element is configured to sense at least one of load conditions, wear, thermal degradation, physical damage and chemical incompatibility, and is coupled to data processing circuitry adapted to signal that an environmental change has occurred or that a structural failure of the seal is impending.

\* \* \* \* \*